(12) United States Patent
Genger et al.

(10) Patent No.: US 9,078,989 B2
(45) Date of Patent: Jul. 14, 2015

(54) APPLICATORS FOR A NASAL CANNULA

(75) Inventors: Harald Genger, Bad Rappenau (DE); Heide Walther, Jena (DE)

(73) Assignee: TNI MEDICAL AG, Würzburg (DE)

( * ) Notice: Subject to any disclaimer, the term of this patent is extended or adjusted under 35 U.S.C. 154(b) by 521 days.

(21) Appl. No.: 12/858,686

(22) Filed: Aug. 18, 2010

(65) Prior Publication Data

US 2011/0073116 A1 Mar. 31, 2011
US 2014/0166021 A9 Jun. 19, 2014

Related U.S. Application Data

(63) Continuation of application No. PCT/DE2009/050008, filed on Feb. 20, 2009.

(30) Foreign Application Priority Data

Feb. 21, 2008 (DE) .................... 10 2008 010 475

(51) Int. Cl.
*A61M 16/20* (2006.01)
*A61M 16/06* (2006.01)

(52) U.S. Cl.
CPC ....... *A61M 16/0666* (2013.01); *A61M 16/0672* (2014.02); *A61M 16/0677* (2014.02); *A61M 16/208* (2013.01); *A61M 2210/0618* (2013.01)

(58) Field of Classification Search
CPC ............... A61M 16/0666; A61M 2210/0618; A61M 16/0672
USPC ........... 128/200.24, 203.22, 205.29, 206.11, 128/206.18, 207.13, 207.18
See application file for complete search history.

(56) References Cited

U.S. PATENT DOCUMENTS

| | | | | |
|---|---|---|---|---|
| 4,782,832 A * | 11/1988 | Trimble et al. | .......... | 128/207.18 |
| 4,818,320 A * | 4/1989 | Weichselbaum | .............. | 156/227 |
| 4,915,105 A * | 4/1990 | Lee | .......................... | 128/205.27 |
| 5,533,506 A * | 7/1996 | Wood | ....................... | 128/207.18 |
| 6,478,026 B1 * | 11/2002 | Wood | ....................... | 128/207.18 |
| 6,644,315 B2 * | 11/2003 | Ziaee | ....................... | 128/206.21 |
| 2002/0170563 A1 * | 11/2002 | Japuntich et al. | ......... | 128/206.12 |
| 2002/0185133 A1 * | 12/2002 | Japuntich et al. | ......... | 128/206.12 |
| 2003/0079749 A1 * | 5/2003 | Strickland et al. | ....... | 128/203.22 |
| 2005/0028822 A1 * | 2/2005 | Sleeper et al. | ............ | 128/207.18 |
| 2005/0028823 A1 * | 2/2005 | Wood | ....................... | 128/207.18 |
| 2005/0155607 A1 * | 7/2005 | Martin et al. | ............ | 128/207.13 |
| 2006/0124131 A1 * | 6/2006 | Chandran et al. | ......... | 128/206.28 |

* cited by examiner

*Primary Examiner* — Loan H Thanh
*Assistant Examiner* — Andrew S Lo
(74) *Attorney, Agent, or Firm* — McGlew and Tuttle, P.C.

(57) ABSTRACT

The invention relates to an applicator for a nasal cannula, comprising a body (11) enclosing a hollow space (22). The applicator further comprises tube connections (20, 21) for supplying a respirable gas into the hollow space (22). The applicator further comprises prongs (18, 19) for administering the respirable gas into the nostrils of a person. A valve (15, 16, 17, 38, 42) is located in a wall of the body (11) so that respirable gas can flow from the outside through the valve into the hollow space (22), but not in the reverse direction. The invention further relates to an applicator having a top of sealing cones (23, 24), wherein the sealing cones (23, 24) may be provided with rim-shaped sealing lips on their side facing away from the body (11), which produce a tight seal with the inner wall of the respective nostril.

12 Claims, 3 Drawing Sheets

APPLICATORS FOR A NASAL CANNULA

FIELD OF THE INVENTION

The field of the invention relates to applicators for nasal cannulae of the type defined in the preambles of the independent patent claims.

The invention relates to the field of nasal cannulae, which are used for pneumatically splinting the respiratory tract.

DISCUSSION OF RELATED ART

In the CPAP therapy (Continuous Positive Airway Pressure Therapy) a patient is supplied via a nose mask with a continuous positive airway pressure relative to the ambient air pressure. This positive airway pressure, if chosen appropriately, ensures that the upper respiratory tract remains completely opened during the whole night, so that no obstructive respiratory disorders occur. One also talks about pneumatically splinting the respiratory tract. The necessary positive airway pressure depends, inter alia, on the sleep phase and the position of the body of the sleeping person. In order to limit the positive airway pressure, which is perceived as unpleasant, to the necessary amount a therapy apparatus (AutoCPAP) is disclosed in WO 02/083221 A2, which adjusts the positive airway pressure automatically, thereby adapting it to the sleep phase and the position of the body.

In order to facilitate the breathing, moreover, BiPAP apparatus and multilevel apparatus have been developed. These apparatus have the property to support the patient's breathing by reducing the positive airway pressure as he is exhaling and by increasing the positive airway pressure again as he is inhaling. That is, these apparatus work with at least two pressure levels. Such apparatus are known, for instance, from DE 691 32 030 T2 and WO 02/26283 A2.

Furthermore, oxygen nasal cannulae for the oxygen treatment are known from the prior art. By means of the oxygen nasal cannula air at an increased oxygen partial pressure (>210 mbar) or pure oxygen is administered into the patient's nose. An oxygen treatment is carried out, for instance, in case of an acute or chronic hypoxemia resulting from a respiratory or cardiovascular disorder (myocardial infarction, shock) or certain intoxications caused, for instance, by carbon monoxide, carbon dioxide, coal gas or smoke.

The use of oxygen nasal cannulae in an anti-snore apparatus is known from WO 02/062413 A2. In this context oxygen nasal cannulae are designated as nasal cannulae. WO 02/062413 A2 further discloses nasal cannulae having integrated jet pumps, which are illustrated in FIGS. 4 and 5 of 02/062413 A2.

US 2003/0079749 A1 and WO 2006/072231 A2 describe nasal cannulae whose nose pieces have rounded edges. The air sweeps past these edges, thereby largely avoiding hissing and whistling noises.

FR 2 827 778 discloses an apparatus which is designated as a monolithic part and resembles the nose part of a nasal cannula. The apparatus serves to support a patient's respiration without or with insufficient spontaneous respiration through the nostrils. The dimensions are adapted to premature infants. Distal, tubular elements project into the nostrils. Foamed discs around the tubular elements serve as a resilient stop. In another embodiment the tubular elements are placed in two dome-shaped sleeves which are connected by a bridge on the side of the sleeves facing away from the nose. Two ducts are supplied with a respirable gas in parallel. A capillary tube serves as a pressure probe. At the beginning of an inspiration phase a supply device receives through the capillary tube a pressure drop and can supply the patient with a continuous or pulse-shaped jet of respirable gas. After an inspiration phase the supply device is instructed by the pressure transmitted through the capillary tube to stop the gas supply. Thus, the patient is able to freely exhale.

SUMMARY OF THE INVENTION

It is the object of the invention to provide improved applicators for nasal cannulae.

This object is achieved with the teaching of the independent claims.

Preferred embodiments of the invention are defined in the dependent claims.

A valve in a wall of the body of the applicator, with the valve allowing gas only from the ambiance to flow into the body of the applicator, has the surprising advantage that the user is not exposed to the risk of suffocating if the connected compressor is defective.

A top slipped over the prongs can adapt the outer shape of the prongs in a surprisingly simple fashion to the inner shape of the nostrils of a patient. Thus, merely the small, relatively simply shaped top has a patient-specific shape, and not the large nasal cannula whose shape is relatively complicated. Hence, greater quantities of the nasal cannula and, thus, a reduction of costs are achieved.

A bridge between the two sealing cones of the top on their side facing the body (11) prevents a single sealing cone from getting lost. Furthermore, in a surprisingly simple fashion, the sealing cones are prevented from turning out of position on the prongs. Finally, the bridge also prevents the top from unintentionally getting pulled off from the prongs.

Rim-shaped sealing lips on the side of the sealing cones facing away from the body of the applicator produce a comfortable tight connection with the inner wall of the respective nostril.

As the sealing cones are partially hollow between an inner part and an outer cone so as to allow a gas flow between the inner cylinder (31, 32) and the respective outer cone (33, 34) parallel to the inner cylinder (31, 32), the additional air resistance in the nostril is kept small by the applicator.

It is an advantage of the membrane-loaded outlets on the body-sided end of the outer cones that the user does not inhale again the exhaled, used air. Moreover, the choice of the rigidity of the shim-shaped membranes allows an adjustment of the positive airway pressure produced by the applicator, which facilitates the control of the connected compressor.

The collar on the nose-sided end of the prongs advantageously prevents the top from unintentionally getting pulled off.

The cover permits a simple mounting of the flexible membrane.

BRIEF DESCRIPTION OF THE DRAWINGS

A preferred embodiment of the invention with reference to the accompanying drawings shall be explained in more detail below. In the drawings.

LIST OF REFERENCE NUMBERS

Figure 1:
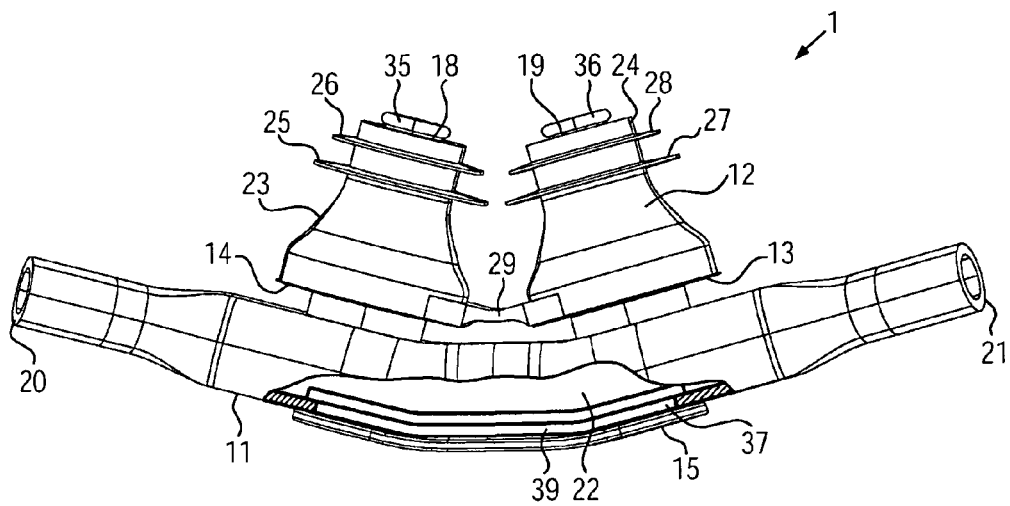
FIG. 1 shows a front view of an applicator according to the invention.

1 applicator
11 body
12 top
13, 14 membrane
15 cover
16, 17 membrane
18, 19 prong
20, 21 tube connection
22 hollow space
23, 24 sealing cone
25, 26, 27, 28 sealing lip
29 bridge
30 rib
31, 32 inner cylinder
33, 34 outer cone
35, 36 collar
37 oblong hole
38 aperture
39 groove
40, 41 frusto-conical prolongation
42 braces

DETAILED DESCRIPTION OF THE PREFERRED EMBODIMENT

Figure 5:
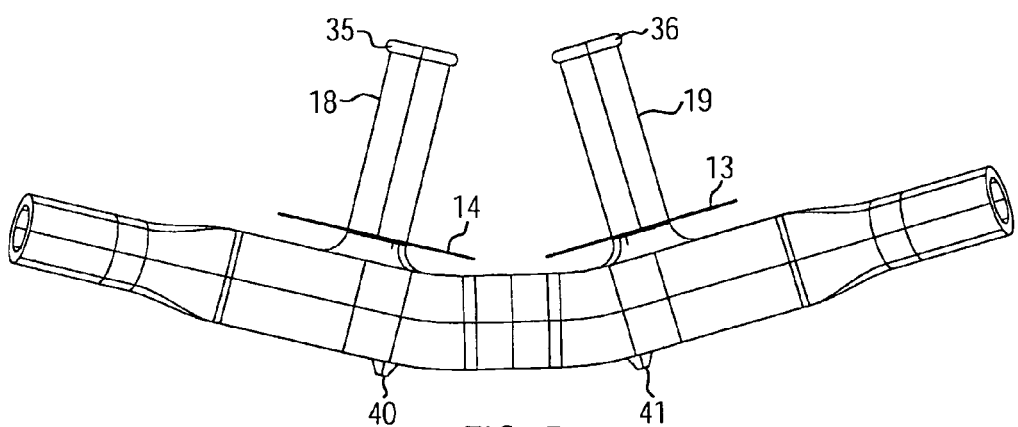
FIG. 5 shows the front view of FIG. 1 without top and cover.

FIG. 1 shows a front view of the applicator 1 according to the invention. The applicator 1 is mainly formed of a body 11 that is connected to a compressor by two tube connections 20, 21 via a non-illustrated tube loop. The body 11 has two prongs 18, 19 over which a top 12 has been slipped. The top 12 is substantially comprised of two sealing cones 23, 24. Synonyms or equivalents of a compressor are a pump, a compressed air source, a supply device or a blower. In FIG. 1 substantially only the collars 35, 36 of the prongs 18, 19 can be seen. The prongs 18, 19 without the sealing cones 23, 24 are shown in FIG. 5.

The sealing cones according to FIG. 1 are adapted to the inner shape of the nostrils of a user at the top, i.e. on their nose-sided end away from the body. The sealing cones are, in fact, slightly smaller than the openings of the user's nostrils. This small gap is bridged and sealed by sealing lips 25, 26, 27 and 28. The sealing lips 25, 26, 27 and 28 themselves have approximately the shape of a circumferential surface of a very flat cone. This means that they extend from the inward top to the outward bottom. As a result of this shape the sealing cones can be easily introduced into the nose and represent a small resistance to prevent the applicator from slipping out of the nose.

The sealing cones 23, 24 are connected to each other on their lower end, which is away from the nose and close to the body, by a bridge 29 in order to prevent the sealing cones 23, 24 from being pulled off from the prongs 18, 19 too easily and to prevent the sealing cones 23, 24 from being turned out of position relative to the body 11 and the user's nostrils.

Figure 6:
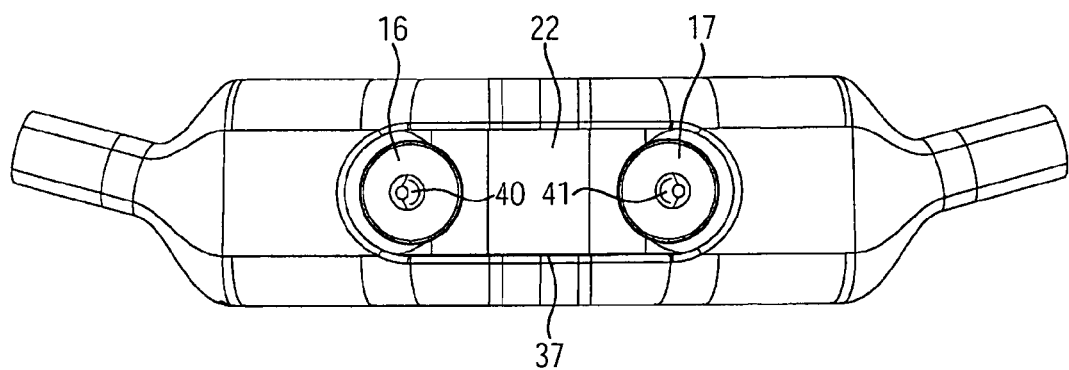
FIG. 6 shows the bottom view of FIG. 4 without top and cover.
Figure 7:
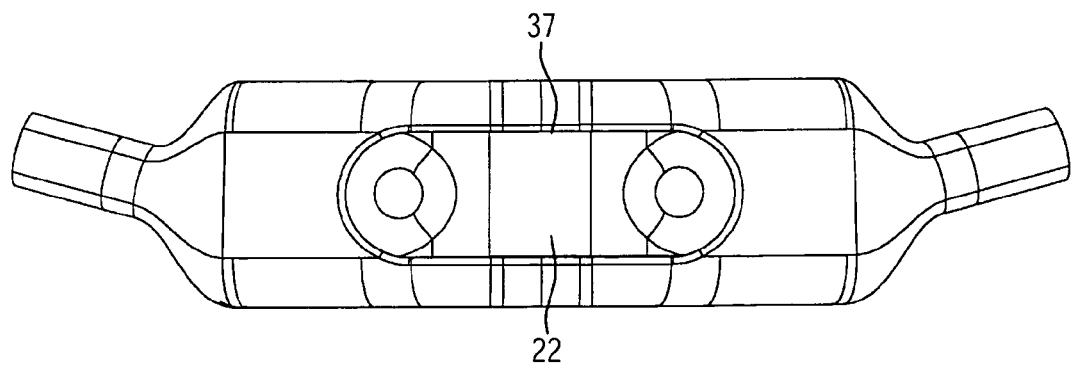
FIG. 7 shows the bottom view of FIG. 6 without membranes.

On the side of the body 11 opposite the prongs 18, 19 the body 11 is provided with an oblong hole 37, which is easy to recognize in FIGS. 6 and 7. The oblong hole 37 is sealed by a cover 15 which forms two valves together with the membranes 16, 17 (see FIG. 4). The cover has a circumferential groove 39 on its outer edge, which engages with the wall of body 11 that limits the oblong hole 37. Hence, the cover 15 is clamped relative to the wall of body 11 and seals the oblong hole 37 in a gas-tight manner.

The body 11 encloses a hollow space 22. Especially the inner surfaces of the body 11 do not have any sharp edges. Rather are all edges rounded off so as to minimize flow noises. As the wall of the body 11 has approximately the same thickness these rounded portions can also be seen on the outside of body 11.

Figure 2:
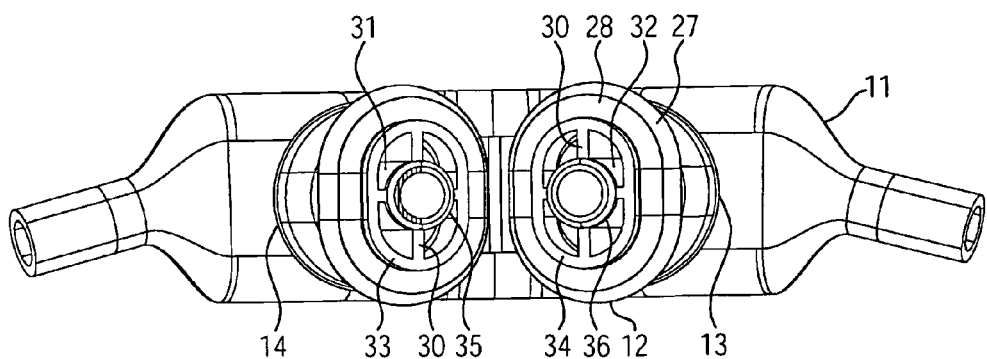
FIG. 2 shows a top view of an applicator according to the invention.

FIG. 2 shows a top view of an applicator according to the invention. It can be recognized that the sealing cones 23, 24 are comprised of outer cones 33 and 34, inner cylinders 31 and 32 and ribs 30 mechanically connecting the outer cones 33, 34 to the inner cylinders 31, 32. The outer surfaces of the prongs 18, 19 are approximately cylindrical and define a fit with the inner surfaces of the inner cylinders 31, 32.

In operation respirable gas compressed by a compressor flows from the tube connections 20, 21 through the hollow space 22 through the prongs 18, 19 into the nose of a user. Vice versa, exhaled air flows through the sealing cones 23, 24, i.e. between the inner cylinders 31, 32 and the outer cones 33, 34 past the ribs 30, through slightly downwardly bent membranes 13 and 14 to the outside. This means that the user practically no longer inhales any exhaled air.

As shown in FIG. 1, the outer cones 33, 34 end slightly above the body 11, while the inner cylinders 31, 32 come up to the body 11. The openings between the inner cylinders 31, 32 and the outer cones 33, 34 are sealed by the membranes 13, 14. However, if there is a certain positive airway pressure between the inner cylinders 31, 32 and the outer cones 33, 34, as is the case during exhaling, the membranes 13, 14 are bent slightly downwardly so that exhaled air can escape to the atmosphere. The administered positive airway pressure can be adjusted by means of the hardness of the membranes 13, 14 and the size of the membranes 13, 14 together with the size of the body-sided outlets of the sealing cones 23, 24. The inner cylinders 31, 32 have at least one step which presses the membranes 13, 14 against the outer cones 33, 34. In another embodiment the inner cylinders 31, 32 may also be provided with grooves which fix the vertical positions of the membranes relative to the outer cones 33, 34.

Figure 3:
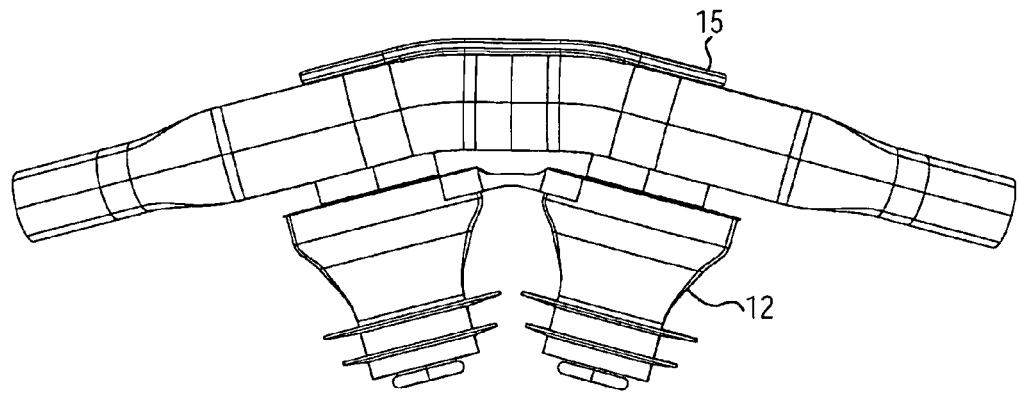
FIG. 3 shows a rear view of an applicator according to the invention.

FIG. 3 shows a rear view of an applicator according to the invention.

Figure 4:
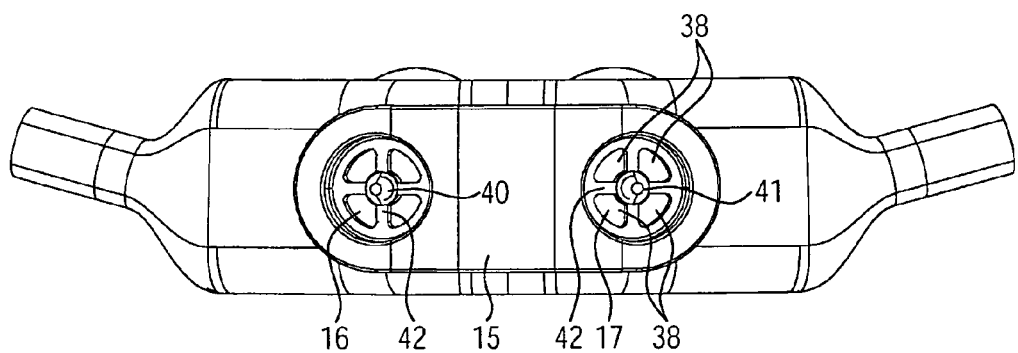
FIG. 4 shows a bottom view of an applicator according to the invention.

FIG. 4 shows a bottom view of an applicator according to the invention. In this view one can recognize the two valves in the cover 15. The cover 15 has two round cavities each partially closed by a cross. Between the braces 42 of the cross four approximately quadrant-shaped apertures 38 remain in the cover 15. The apertures 38 are sealed from inside by the flexible membranes 16, 17 so that air can enter the hollow space 22 from the outside, while it cannot escape from inside out of the hollow space 22 through the apertures 38 to the outside. FIG. 6 shows the same view as FIG. 4, however, without illustrating the cover 15, so that the membranes 16, 17 seem to float in the air. The two valves allow a user to inhale even if no respirable gas is supplied through the tube connections 20, 21 in the event of a failure of the compressor.

The two membranes 16, 17 each have a frusto-conical prolongation 40 and 41 in the center which projects towards the viewer in FIGS. 4 and 6. The frusto-conical prolongations are connected to the actual membranes by cylindrical sections. The cylindrical sections have a diameter smaller than the largest diameters of the frusto-conical prolongations, so that a groove is defined between each frusto-conical prolongation and the respective membrane. This groove rests in a central hole in the braces 42 of the crosses in the cavities of the cover 15.

FIG. 5 shows a view similar to that of FIG. 1, however, without illustrating the top 12 with the sealing cones 23, 24 and the cover 15. That is, the cylindrical prongs 18, 19, the collars 35, 36 as well as the membranes 13, 14 are easier to recognize. On the bottom side, the frusto-conical prolongations 40, 41 of the membranes 16, 17 project out of the oblong hole 37.

FIG. 7 shows a view similar to that of FIG. 6, however, without illustrating the membranes 16 and 17. In this view, the oblong hole 37 allows a sight through the hollow space 22 to the inside of the rounded junctions between the prongs 18, 19 and the rest of the body 11. On the inside the radius of the rounded portion is approximately as large as the inner diameter of the prongs 18, 19. One can see in FIG. 5 that the radius of this rounded portion on the outside is approximately half as large as on the inside. That is because the wall thickness in the region of the prongs 18, 19 is approximately half the size as in the rest of the body 11.

In can be recognized in FIGS. 2, 4, 6 and 7 that the body is substantially broader than the tube connections 20, 21. Apart from the purpose of providing space for the cover 15 and the valves located in the cover 15 this measure also has the purpose of reducing the flow velocity of the gas in the junction region between the prongs 18, 19 and the body 11 by enlarging the cross-section, thereby reducing flow noises.

The invention was explained in more detail by means of preferred embodiments above. A person skilled in the art will appreciate, however, that various alterations and modifications may be made without departing from the spirit of the invention. Therefore, the scope of protection will be defined by the following claims and their equivalents.

The invention claimed is:

1. An applicator for a nasal cannula, comprising:
    a body enclosing a hollow space;
    a first tube connection and a second tube connection for supplying a respirable gas into the hollow space, the first tube connection and the second tube connection being integrally formed on the body;
    a first prong and a second prong for administering the respirable gas into the nostrils of a user, the first prong and the second prong being integrally formed on the body;
    a valve in a wall of the body, the valve being constructed such that the respirable gas, independent of the respirable gas supplied via the first tube connection and the second tube connection, can flow directly from an outside of the body through the valve into the hollow space and then further to the first prong and the second prong, wherein the valve inhibits gas flow from the hollow space through the valve to the outside of the body; and
    a top that is slipped over the first prong and the second prong for sealing between the first prong and the second prong and an inner wall of a respective nostril, said top being formed of a first sealing cone and a second sealing cone, wherein the first sealing cone and the second sealing cone have on a side facing away from the body a different cross-section area and a different cross-section shape than on a side facing the body, said first sealing cone and said second sealing cone being mechanically connected by a bridge on the side facing the body.

2. Applicator of claim 1, wherein the two sealing cones have one or more rim-shaped sealing lips on the side facing away from the body, which produces a tight seal with an inner wall of a respective nostril.

3. An applicator for a nasal cannula, comprising:
    a body enclosing a hollow space;
    a first tube connection and a second tube connection for supplying a respirable gas into the hollow space, wherein the first tube connection and second tube connection are integrally formed on the body;
    a pair of prongs comprising a first prong and a second prong for administering the respirable gas into nostrils of a user, wherein the first prong and the second prong are integrally formed on the body; and
    a top slipped over the pair of prongs for sealing between the pair of prongs and an inner wall of a respective nostril, wherein the top is formed of sealing cones comprising a first sealing cone and a second sealing cone, wherein the sealing cones have on a side facing away from the body a different cross-section area and a different cross-section shape than on a side facing the body; wherein the sealing cones have one or more rim-shaped sealing lips on a side facing away from the body that produces a tight seal with the inner wall of the respective nostril, wherein each of the two sealing cones further comprises an inner part, an outer cone and ribs, wherein an inner circumferential surface of the inner part forms a fit with an outer circumferential surface of a respective prong, and wherein the ribs mechanically connect the inner part to their respective outer cone to allow a gas flow parallel to the inner part between the inner part and their respective outer cone.

4. An applicator for a nasal cannula, comprising:
    a body enclosing a hollow space;
    a first tube connection and a second tube connection for supplying a respirable gas into the hollow space, the first tube connection and the second tube connection being integrally formed on the body;
    a first prong and a second prong for administering the respirable gas into nostrils of a person, wherein the first and second prongs are integrally formed on the body; and
    a top slipped over the prongs for sealing between the prongs and an inner wall of the respective nostril, wherein the top is formed of a sealing cones, namely a first sealing cone and a second sealing cone, wherein the sealing cones have on a side facing away from the body a different cross-section area and a different cross-section shape than on a side facing the body, wherein each of the two sealing cones further comprise an inner part, an outer cone, and ribs, wherein an inner circumferential surface of the inner part forms a fit with an outer circumferential surface of its respective prong and wherein the ribs mechanically connect the inner part to the respective outer cone to allow a gas flow parallel to the inner part between the inner part and the respective outer cone.

5. The applicator of claim 4, wherein the inner part projects on a body-sided end over an outer cone body-sided end in the direction of the body, the inner part being provided with a circumferential step at the outer cone body-sided end, wherein the circumferential step presses a shim-shaped membrane against the outer cone body-sided end, wherein the shim-shaped membrane seals the opening between the inner part and the outer cone.

6. The applicator according to claim 5, wherein the prongs further comprise a collar on their nose-sided end, wherein an outer diameter of the collar is larger than central openings within the inner part of each of the two sealing cones.

7. An applicator for a nasal cannula, comprising:
    a body enclosing a hollow space;

a first tube connection and a second tube connection for supplying a respirable gas into the hollow space, wherein the first tube connection and second tube connection are integrally formed on the body;

prongs comprising a first prong and a second prong for administering the respirable gas into the nostrils of a user, wherein the first prong and the second prong are integrally formed on the body, wherein the prongs further comprise a collar on a nose-sided end of the prongs; and a top slipped over the prongs for sealing between the prongs and an inner wall of a respective nostril, wherein an outer diameter of the collar is larger than nose-sided ends of central openings formed within an inner part of two sealing cones, said top being slipped over the prongs such that the nose-sided ends of the central openings of the two sealing cones are placed below a body-sided end of the collar.

8. The applicator according to claim 7, wherein the body further comprises a hole embedding a cover, wherein the cover has a groove, wherein an edge of the hole of the body engages into the groove, wherein the cover has an aperture sealed by a flexible membrane on a side facing the hollow space to allow a gas flow from an ambiance through the aperture in the cover into the hollow space, wherein the flexible membrane prevents gas flow from the hollow space through the aperture in the cover into the ambiance.

9. The applicator according to claim 7, wherein each said collar is located at a position above said nose-sided end of one of said central openings.

10. The applicator according to claim 7, wherein each of said two sealing cones comprises an end portion, each said collar being located at a position above said end portion of one of said two sealing cones.

11. The applicator according to claim 7, wherein nose-sided ends of said sealing cones are positioned below said collar.

12. The applicator according to claim 7, wherein each of said two sealing cones comprises a nose-sided end, said nose-sided end of each of said two sealing cones being located at a position below said collar of one of said prongs.

* * * * *